(12) United States Patent
Kroll

(10) Patent No.: US 6,865,420 B1
(45) Date of Patent: Mar. 8, 2005

(54) CARDIAC STIMULATION DEVICE FOR OPTIMIZING CARDIAC OUTPUT WITH MYOCARDIAL ISCHEMIA PROTECTION

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 468 days.

(21) Appl. No.: 10/047,115

(22) Filed: Jan. 14, 2002

(51) Int. Cl.$^7$ ............................................. A61N 1/365
(52) U.S. Cl. ....................................................... 607/25
(58) Field of Search .............................. 607/4–6, 9, 14, 607/17, 25; 600/516, 517, 509, 515

(56) References Cited

U.S. PATENT DOCUMENTS

| | | | |
|---|---|---|---|
| 5,135,004 A | | 8/1992 | Adams et al. ............... 128/696 |
| 5,199,428 A | | 4/1993 | Obel et al. .................. 128/419 |
| 5,203,326 A | * | 4/1993 | Collins ........................... 607/4 |
| 5,282,840 A | | 2/1994 | Kudrlik ........................ 607/28 |
| 5,292,348 A | | 3/1994 | Saumarez et al. .............. 607/5 |

(List continued on next page.)

FOREIGN PATENT DOCUMENTS

WO    WO 00/57781    10/2000    ......... A61B/5/0472

OTHER PUBLICATIONS

Barold, S.S., "Diagnosis of Myocardial Ischemia During Ventricular Pacing", PACE, vol. 23, pp: 1060–1061 (Jun. 2000).

Kleber, Andre G., "ST–segment elevation in the electrocardiogram: a sign of myocardial ischemia", Cardiovascular Research; 45 (1), pp: 111–118 (2000).

Tisdale, Lisa A., et al., "ST Segment Monitoring for Myocardial Ischemia", AACN Clinical Issues in Critical Care Nursing, vol. 4, No. 1, pp: 34–43 (Feb. 1993).

Nabel, Elizabeth G., et al., "Detection of Pacing–Induced Myocardial Ischemia by Endocardial Electrograms Recorded During Cardiac Catherization", JACC, pp: 983–992, (May 1988).

Barold, S. Serge, et al., "Permanent Multisite Cardiac Pacing", PACE, vol. 20, pp: 2725–2729 (Nov. 1997).

Wagner, Galen S., Marriot's Practical Electrocardiography, 10$^{th}$ Edition, Lippincott Williams & Wilkins, Philadelphia, Chapters 8–9 (2001).

*Primary Examiner*—George Manuel

(57) ABSTRACT

A cardiac stimulation device and method detect myocardial ischemia and provide a response for alleviating the ischemia. Myocardial ischemia is detected by identifying changes in the ST-segment of the intracardiac electrogram (EGM) sensed using large sensing electrode surfaces created by electrically coupling one or more cardiac electrodes or by using larger surface area shocking coils. Myocardial ischemia monitoring is performed when stimulation parameters are adjusted for increasing cardiac output, causing an increased metabolic demand to be placed on the myocardium itself. When myocardial ischemia is detected, stimulation parameters are re-adjusted to reduce the demand placed on the myocardium and thereby alleviate the ischemia.

72 Claims, 8 Drawing Sheets

U.S. PATENT DOCUMENTS

| | | | |
|---|---|---|---|
| 5,313,953 A | 5/1994 | Yomtov et al. | 128/696 |
| 5,388,578 A | 2/1995 | Yomtov et al. | 128/642 |
| 5,497,780 A | 3/1996 | Zehender | 128/696 |
| 5,531,768 A * | 7/1996 | Alferness | 607/6 |
| 5,701,906 A | 12/1997 | Alcidi et al. | 128/696 |
| 5,728,281 A | 3/1998 | Holmström et al. | 204/403 |
| 5,740,811 A | 4/1998 | Hedberg et al. | 128/697 |
| 5,792,066 A | 8/1998 | Kwong | 600/517 |
| 5,807,272 A | 9/1998 | Kun et al. | 600/547 |
| 6,016,443 A | 1/2000 | Ekwall et al. | 600/519 |
| 6,021,350 A | 2/2000 | Mathson | 607/17 |
| 6,108,577 A | 8/2000 | Benser | 600/517 |
| 6,112,116 A | 8/2000 | Fischell et al. | 600/517 |
| 6,115,628 A | 9/2000 | Stadler et al. | 600/517 |
| 6,128,526 A | 10/2000 | Stadler et al. | 600/517 |
| 6,129,744 A | 10/2000 | Boute | 607/25 |
| 6,233,486 B1 | 5/2001 | Ekwall et al. | 600/17 |
| 6,256,538 B1 | 7/2001 | Ekwall | 607/17 |
| 6,264,606 B1 | 7/2001 | Ekwall et al. | 600/300 |
| 6,272,379 B1 | 8/2001 | Fischell et al. | 607/5 |
| 6,317,625 B1 | 11/2001 | Olson et al. | 600/509 |
| 6,324,421 B1 | 11/2001 | Stadler et al. | 600/509 |
| 6,368,284 B1 | 4/2002 | Bardy | 600/508 |
| 6,381,493 B1 * | 4/2002 | Stadler et al. | 607/9 |
| 6,501,983 B1 | 12/2002 | Natarajan et al. | 600/517 |
| 6,514,195 B1 | 2/2003 | Ferek-Petric | 600/17 |
| 6,532,381 B2 | 3/2003 | Bayer et al. | 600/515 |
| 2002/0143262 A1 | 10/2002 | Bardy | 600/508 |
| 2003/0045805 A1 | 3/2003 | Sheldon et al. | 600/513 |
| 2003/0045908 A1 | 3/2003 | Condie et al. | 607/9 |

\* cited by examiner

CARDIAC STIMULATION DEVICE FOR OPTIMIZING CARDIAC OUTPUT WITH MYOCARDIAL ISCHEMIA PROTECTION

FIELD OF THE INVENTION

The present invention relates generally to an implantable cardiac stimulation device capable of optimizing cardiac output, and in particular, is directed to detecting and protecting against myocardial ischemia.

BACKGROUND OF THE INVENTION

Abnormal heart rhythms are successfully treated by artificial cardiac pacing using implantable cardiac stimulation devices, including pacemakers and implantable defibrillators, that deliver rhythmic electrical pulses or other anti-arrhythmia therapies to the heart. Early pacemakers delivered stimulation pulses to the heart at a fixed rate. Fixed rate pacing, however, is not physiological in that periods of increased activity or metabolic demand are not accompanied by the normal physiological rise in heart rate. Rate-responsive pacemakers were, therefore, introduced. Rate-responsive pacemakers employ sensors that indicate changes in physical activity or metabolic demand. One commonly used sensor is a piezoelectric element that responds to changes in physical activity. Other sensors used in rate-responsive pacemakers measure blood oxygen levels, pH of the blood, minute volume, respiration rate, or tidal volume. As an increase in the patient's systemic metabolic demand is detected by one or more sensors, device operating parameters controlling the manner in which stimulation is delivered to the heart are adjusted such that the cardiac output better meets the patient's metabolic need. Typically, the stimulation rate and often the interval between atrial contraction and ventricular stimulation are adjusted.

Cardiac pacing of two, three or even all four heart chambers has been found to be potentially beneficial to patients suffering from congestive heart failure. Multi-site stimulation is aimed at resynchronizing the contractions of the heart chambers in an attempt to improve the working efficiency of the heart and the decreased cardiac output associated with congestive heart failure. Thus, cardiac stimulation devices have been proposed that are capable of sensing a parameter correlated to cardiac output. The device then adjusts stimulation parameters in a way that maximizes cardiac output to improve the well-being of a patient in heart failure.

Both rate responsive cardiac stimulation devices and stimulation devices directed at treating congestive heart failure, or the combination of both, improve patient benefit by optimizing stimulation parameters according to the systemic need for increased cardiac output. However, in adjusting stimulation parameters, particularly increasing stimulation rate, the metabolic demand placed on the myocardium itself is increased. Demand-induced myocardial ischemia may result, particularly in patients with coronary artery disease or ischemic cardiomyopathy.

An increased heart rate results mainly in a shortening of the diastolic phase, which is the period during which oxygen is supplied to the heart. An increased stimulation rate will consequently worsen the situation for an ischemic patient. Symptomatic ischemia, that is ischemia resulting in angina pectoris, will force the patient to rest because of the associated pain. The heart rate will decrease allowing the heart to recover from the ischemic episode given a myocardial infarct has not already occurred. However a large portion of cardiac ischemia may be silent, i.e., a state of ischemia that the patient is not aware of because of an absence of symptoms. Prolonged ischemia will result in irreversible injury to the myocardial tissue.

Myocardial ischemia can be detected by observing changes in the ST-segment of an electrocardiogram. Elevation of the ST-segment in relation to the PQ- and TP-segments is a known indication of myocardial ischemia. Thus, ST-segment elevation may be used as a diagnostic marker of myocardial ischemia during cardiac stimulation.

ST-segment changes may be observed using both surface electrocardiogram (ECG) leads or implanted cardiac electrogram (EGM) leads that are located on or in the heart. The sensitivity of ST-segment changes as a marker of myocardial ischemia is dependent on the number and location of the electrodes. ST-segment elevation observed on an EGM using endocardial leads during cardiac catheterization has been found to indicate myocardial ischemia earlier than changes observed on a surface ECG.

Thus, it would be advantageous to use the heart electrodes implanted in, or in proximity to the heart in connection with a cardiac stimulation device for monitoring for changes in the EGM signal that are indicative of myocardial ischemia. Early, reliable detection of myocardial ischemia that prevents sustained, potentially life-threatening, ischemic episodes would enhance the benefit provided to a patient by cardiac stimulation devices. Therefore, it would be desirable to provide a device and method for detecting ST-segment changes with high sensitivity. Furthermore, it is desirable to provide a device capable of responding to detected myocardial ischemia in a way that alleviates the ischemia.

SUMMARY OF THE INVENTION

A method for detecting and alleviating myocardial ischemia in an implantable cardiac stimulation device is provided, and is capable of adjusting stimulation parameters for maximizing cardiac output in response to a patients metabolic need. Myocardial ischemia is preferably detected by identifying changes in the ST-segment of the intracardiac electrogram (IEGM) using large sensing electrode surfaces created by electrically coupling one or more cardiac electrodes or by using larger surface area shocking coils. When myocardial ischemia is detected, stimulation parameters are adjusted to reduce the demand placed on the myocardium and thereby alleviate the ischemia.

When operating according to a preferred embodiment, two electrodes located on a coronary sinus lead are coupled together to operate as a single, larger coronary sinus sensing surface. Two electrodes located on a right ventricular lead are also coupled together to operate as a single, larger right ventricular sensing surface. The coupled electrodes may be selectively connected to sense amplifiers for receiving one or more desired EGM signals.

In a preferred embodiment, EGM signals may be obtained from three enhanced surface area, cardiac sensing vectors: 1) the differential signal between the coupled coronary sinus electrodes and the device housing; 2) the differential signal between the coupled right ventricular electrodes and the device housing; and 3) the differential signal between the coupled coronary sinus electrodes and the coupled right ventricular electrodes.

ST-segment changes or T-wave changes from any or all of these signals are then examined for evidence of myocardial ischemia. This may include ST-segment elevation, ST-segment depression, or T-wave inversion. In alternative embodiments, shocking coil electrodes may be used, if available, for sensing EGM signals for the detection of myocardial ischemia.

If myocardial ischemia is detected, stimulation parameter adjustments are made to alleviate the ischemia. Typically, this adjustment will be a reduction in stimulation rate. Other adjustments may include switching from single ventricular stimulation to biventricular stimulation. Such adjustments may be made after a short delay, e.g., 10 to 20 seconds, in case the initial myocardial ischemia detection is based on an ST-segment deviation associated with a postural change or other temporary cause.

The methods described herein thus improve the benefit provided by cardiac stimulation devices capable of adjusting stimulation parameters to optimize cardiac output by also taking into account the demand placed on the myocardium. The methods described provide a sensitive, reliable method for detecting ST-segment changes indicative of ischemia. Through early detection and alleviation of myocardial ischemia, patient benefit is enhanced.

BRIEF DESCRIPTION OF THE DRAWINGS

The various features and the manner of attaining them will be described in greater detail with reference to the following description, claims, and drawings, wherein reference numerals are reused, where appropriate, to indicate a correspondence between the referenced items, and wherein:

DETAILED DESCRIPTION OF PREFERRED EMBODIMENTS

The following description includes a best mode presently contemplated for the device. This description is not to be taken in a limiting sense but is made merely for the purpose of describing the general principles of the device. In the description that follows, like numerals or reference designators will be used to refer to like parts or elements throughout.

The disclosed device and method are directed at detecting and alleviating myocardial ischemia during cardiac stimulation that is automatically adjusted to optimize cardiac output. Thus, the methods described herein are intended to be incorporated in any cardiac stimulation device capable of adjusting stimulation parameters in response to a physiological signal that is related to cardiac output or a change in cardiac output demand according to systemic metabolic need. A general cardiac stimulation device will thus be described in conjunction with FIGS. 1 and 2, in which the myocardial ischemia detection methods described herein could be implemented. It is recognized, however, that numerous variations of such a device exist in which the methods could be implemented.

Figure 1:
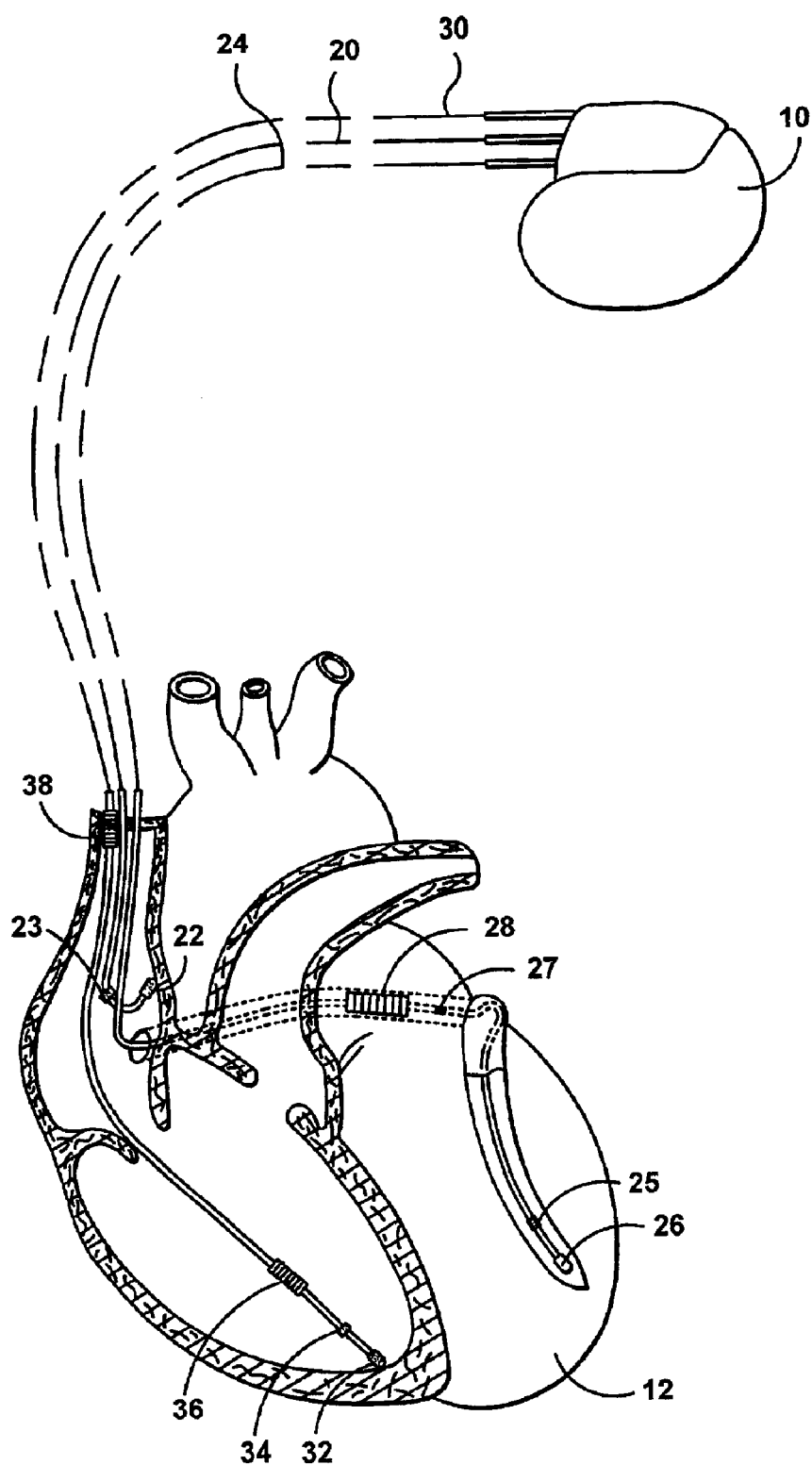
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place at least a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to: receive atrial and ventricular cardiac signals; deliver left ventricular pacing therapy using at least a left ventricular tip electrode 26 for unipolar configurations or in combination with left ventricular ring electrode 25 for bipolar configurations; deliver left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

Figure 2:
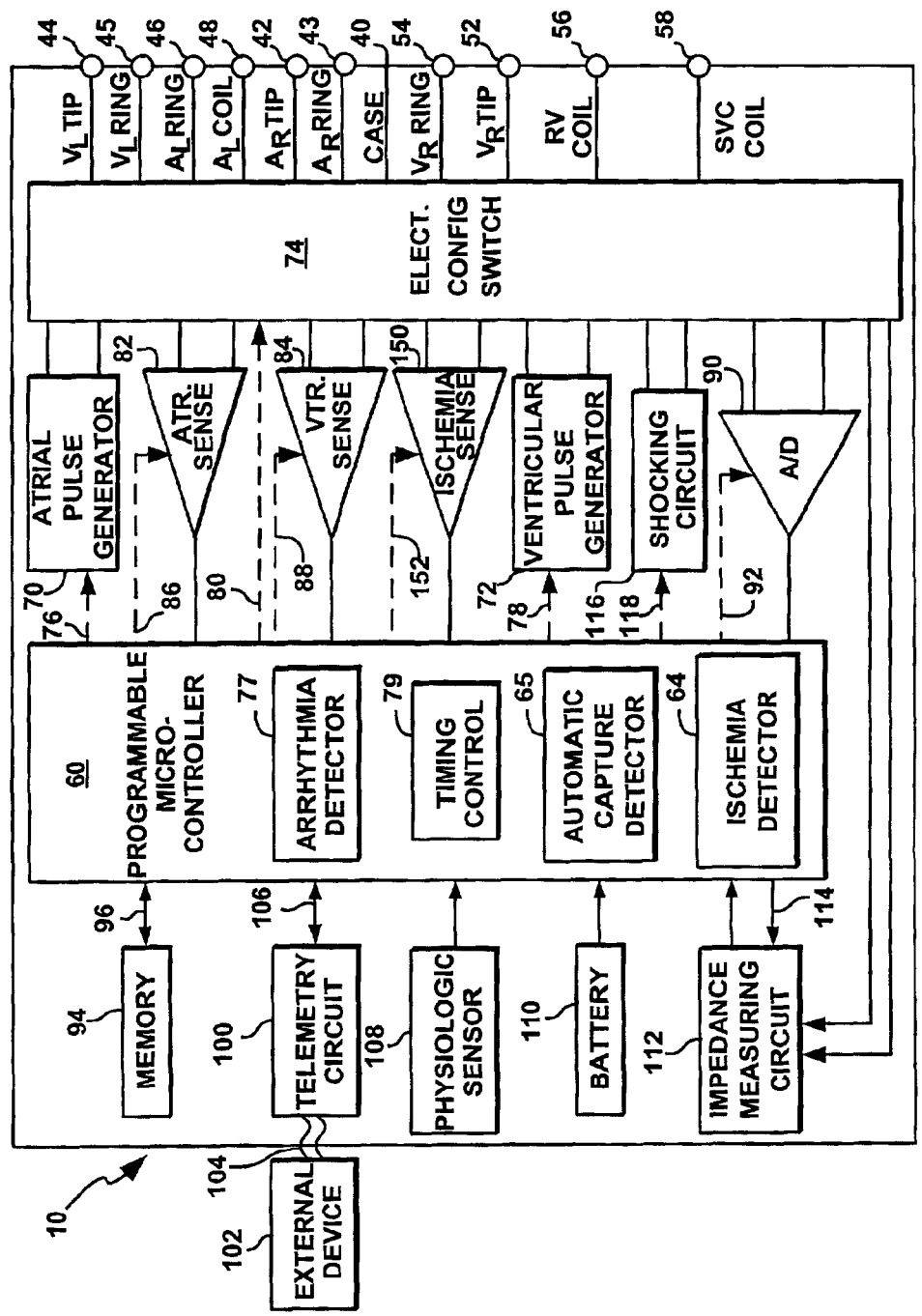
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. The stimulation device 10 is also capable of automatically adjusting stimulation parameters to provide an optimized cardiac output according to a patient's activity level or metabolic demand and/or for the treatment of congestive heart failure. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for defibrillation shocking purposes. In accordance with one embodiment, the housing 40 can be used as the return electrode during sensing of EGM signals for the detection of myocardial ischemia.

The housing 40 further includes a connector having a plurality of terminals 42, 43, 44, 45, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal ($A_R$ TIP) 42 adapted for connection to the atrial tip electrode 22. The connector may also include a right atrial ring terminal ($A_R$ RING) 43 for connection to the right atrial ring electrode 23.

To achieve left chamber sensing, pacing, and shocking, the connector includes at least a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, which are adapted for connection to the left ventricular tip electrode 26, the left ventricular ring electrode 25, the left atrial ring electrode 27, and the left atrial coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interchamber (A—A) delay, or ventricular interchamber (V—V) delay, etc.), as well as to keep track of the timing of refractory periods, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches.

Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

In one embodiment, stimulation device 10 may further include an ischemia sensing circuit 150 dedicated to sensing EGM signals that are evaluated for changes indicative of myocardial ischemia by an ischemia detector 64, included in the microcontroller 60. As it will be described in detail with reference to FIGS. 3 and 4, a desired combination of electrodes may be connected to ischemia sensing circuit 150 through switch 74.

The output of ischemia sensing circuit 150 is connected to the microcontroller 60. The ST-segment of sensed EGM signals is then analyzed by ischemia detector 64 to detect changes in the ST-segment or T-wave amplitude that correspond to myocardial ischemia.

For arrhythmia detection, the stimulation device 10 includes an arrhythmia detector 77 that utilizes the atrial and ventricular sensing circuits 82 and 84 to sense cardiac signals, for determining whether a rhythm is physiologic or pathologic. As used herein "sensing" refers to the process of noting an electrical signal. "Detection" refers to the step of confirming that the sensed electrical signal as the signal being sought by the detector. As an example, "detection" applies to the detection of both proper rhythms (i.e., "R wave" or "R wave") as well as improper dysrhythmias including arrhythmia and bradycardia (e.g., detection of the absence of a proper rhythm.)

The timing intervals between sensed events (e.g. P-waves, R-waves, and depolarization signals associated with fibrillation which are sometimes referred to as "F-waves" or "Fib-waves") are then classified by the arrhythmia detector 77 by comparing them to a predefined rate zone limit (e.g. bradycardia, normal, low rate ventricular tachycardia, high rate ventricular tachycardia, and fibrillation rate zones) and various other characteristics (e.g. sudden onset, stability, physiologic sensors, and morphology, etc.), in order to determine the type of remedial therapy that is needed (e.g. bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes. In one embodiment, data acquisition system 90 may be used to acquire EGM signals for the analysis of changes in the ST-segment for detecting myocardial ischemia.

Advantageously, the data acquisition system 90 may be coupled to the microcontroller 60 or another detection circuitry, for detecting an evoked response from the heart 12 in response to an applied stimulus, thereby aiding in the detection of "capture". In the embodiment shown in FIG. 2, the microcontroller 60 includes an automatic capture detector 65 that searches for an evoked response signal following a stimulation pulse during a "detection window" set by timing control circuitry 79.

The microcontroller 60 enables the data acquisition system 90 via control signal 92 to sample the cardiac signal that falls in the capture detection window. The sampled signal is evaluated by automatic capture detector 65 to determine if it is an evoked response signal based on its amplitude, peak slope, morphology or another signal feature or combination of features. The detection of an evoked response during the detection window indicates that capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 further includes a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various stimulation parameters (such as rate, AV Delay, V—V Delay, etc.) at which the atrial and ventricular pulse generators 70 and 72 generate stimulation pulses.

While the physiologic sensor 108 is shown as being included within the stimulation device 10, it is to be understood that the physiologic sensor 108 may alternatively be external to the stimulation device 10, yet still be implanted within, or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. Thus, the stimulation device 10 may respond to the patient's systemic demand for increased cardiac output.

Alternatively or additionally, physiologic sensor 108 provides a signal related to cardiac output. The stimulation device 10 may then adjust stimulation parameters in order to optimize cardiac output at any given heart rate.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 $\mu$A, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112 which is enabled by the microcontroller 60 by control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

If it is a function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 byway of a control signal 118. The shocking circuit 116 generates shocking pulses of low (up to 0.5 joules), moderate (0.5–10 joules), or high (11 to 40 joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
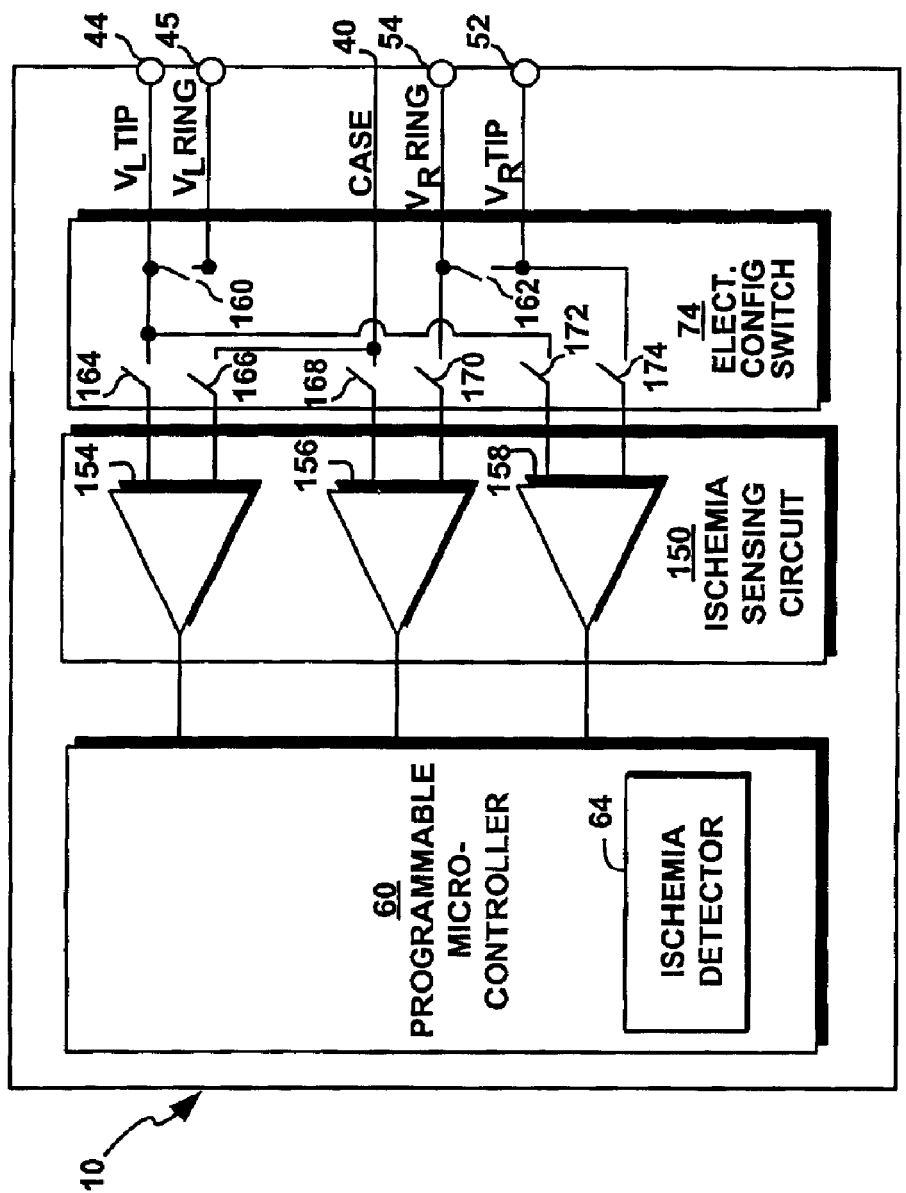
FIG. 3 is a block diagram illustrating an exemplary electrode configuration switch included in the device of FIG. 2, for electrically coupling cardiac electrodes used for sensing EGM signals in the detection of myocardial ischemia.

In FIG. 3, a simplified block diagram illustrates switching circuitry included in electrode configuration switch 74 for connecting a desired set of electrodes to ischemia sensing circuit 150 to facilitate the detection of myocardial ischemia. In the embodiment shown in FIG. 3, two terminals connecting electrodes located on the coronary sinus lead 24, such as terminal 44 connected to left ventricular tip electrode 26 and terminal 45 connected to left ventricular ring electrode 25, are coupled together (i.e., shorted) by a switch 160 included in electrode configuration switch 74, to form a right ventricular (RV) sensing electrode pair. The electrically coupled electrodes located on coronary sinus lead 24 function collectively as a larger sensing surface area over the left ventricle.

Similarly, and as further illustrated in FIG. 3, the right ventricular tip terminal ($V_R$ TIP) 52 and the right ventricular ring terminal ($V_R$ RING) 54, that connect the electrodes located on right ventricular lead 30 could be coupled (or shorted) by switch 162 included in electrode configuration switch 74, to form a left ventricular (LV) sensing electrode pair that functions as a single sensing electrode with an expanded surface area. The coupling of two or more electrodes located on right ventricular lead 30 creates a larger sensing surface area in the region of the right ventricle.

It should be clear that, while in a preferred embodiment, both the LV and the RV sensing electrode pairs have an enhanced sensing surface area, alternative embodiments could include only one of these sensing electrode pairs.

The larger sensing areas in the region of the right and left ventricles enable a more sensitive detection of myocardial ischemia than a single sensing electrode with a smaller surface area. While the smaller sensing surface area strongly favors the detection of local potentials, shorting the electrode pair (or pairs) results in a simulated large electrode with enhanced ability to detect remote myocardial ischemia. This is important since the myocardial ischemia begins in the endocardial surface, which is about 2 cm away from the coronary sinus lead (also referred to as LV lead) 24 which extends in an epicardial vein.

A series of switches 164, 166, 168, 170, 172, an 174 included in electrode configuration switch 74 allow the coupled coronary sinus electrodes, the coupled right ventricular electrodes and the device housing 10 to be connected to ischemia sensing circuit 150 in any combination. Ischemia sensing circuit 150 may employ one or more low power, precision amplifiers with programmable gain and automatic gain or sensitivity control, and bandpass filtering to selectively sense the ST-segment of the EGM.

In the embodiment shown in FIG. 3, ischemia sensing circuit 150 includes three sense amplifiers 154, 156, and 158 for sensing the differential signal between: 1) the coupled coronary sinus electrodes and housing 10; 2) the coupled right ventricular electrodes and device 10; and 3) the coupled coronary sinus electrodes and the coupled right ventricular electrodes, respectively.

While one configuration is depicted in FIG. 3, numerous EGM sensing configurations that employ various combinations of electrically coupled electrodes could be selected depending on the number of electrodes available and leads used.

The outputs of the three amplifiers 154, 156, and 158 are connected to microcontroller 60 to be analyzed by ischemia detector 64. The ST-segment of the EGM may be depressed or elevated relative to the PQ-segment or the TP-segment during myocardial ischemia depending on the sensing configuration and whether the ischemia is caused by increased metabolic demand or insufficient myocardial blood flow. The T-wave may become inverted during myocardial ischemia.

Figure 7:
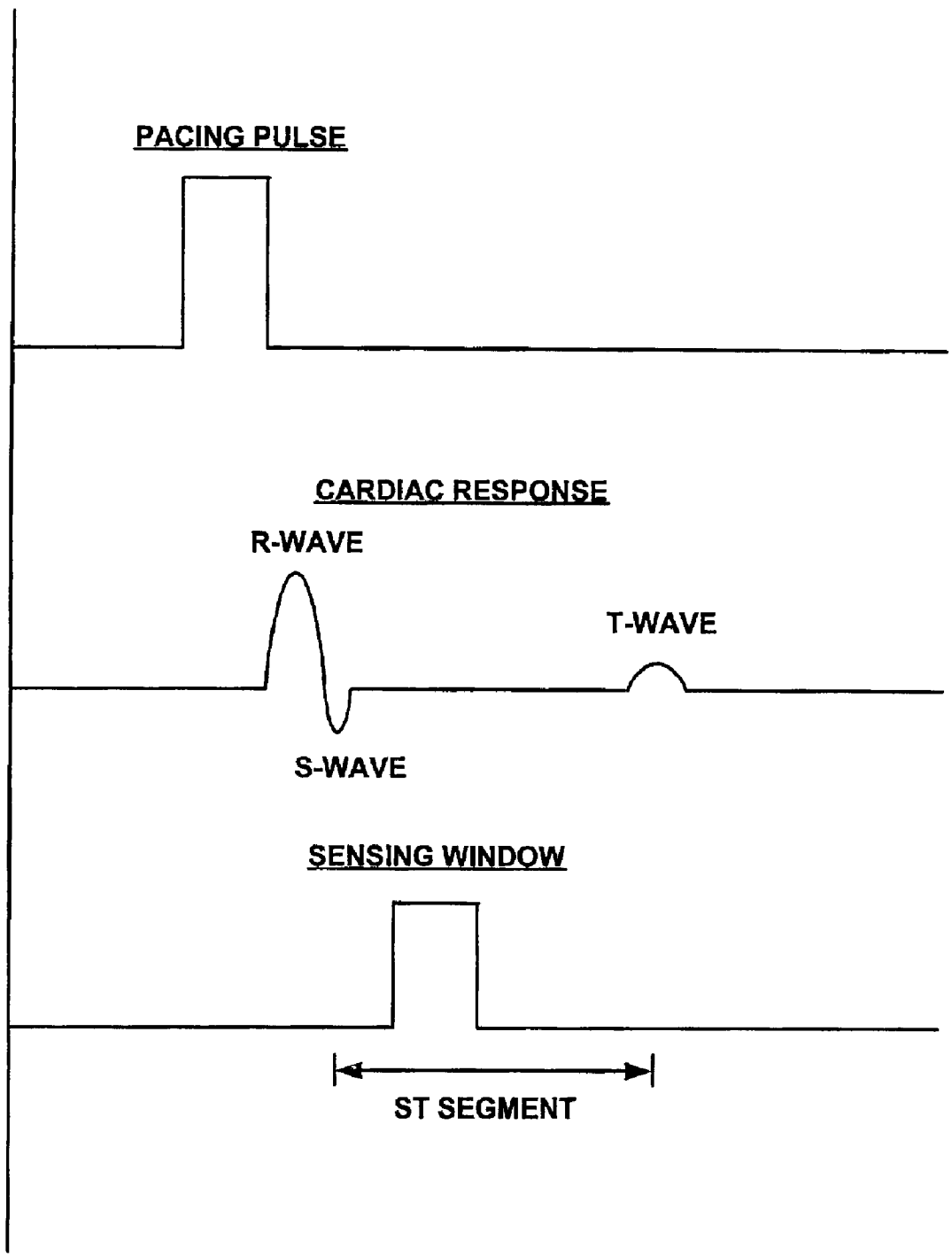
FIG. 7 illustrates three curves: the first curve shows a pacing pulse; the second curve shows a cardiac response with an R-wave followed by a T-wave; and the third curve shows a sensing window within an ST segment, during which the voltage between the RV pair sensing electrode pair and the LV sensing electrode pair is averaged.

The three EGM signals received from ischemia sensing circuit 150 are therefore processed in any combination to confirm the presence or absence of ischemia based on predetermined criteria defining expected deviations of the ST-segment. With further reference to FIG. 7, an exemplary method of processing the sensed signals, or combination of signals, to confirm ischemia would be to detect the R-wave and T-wave; measure the voltage at a midpoint between these waves, and, if the midpoint has changed more than, for example, 10% plus 1 mV from the low rate baseline, the algorithm confirms the occurrence of ischemia.

In a preferred embodiment, the coupling of the sensing electrodes pairs, to form one or more electrodes with expanded sensing surface areas, takes place for the duration of the sensing window illustrated in FIG. 7. This sensing window can extend from a minimal predetermined or programmable value, to the full length of the ST segment.

Figure 4:
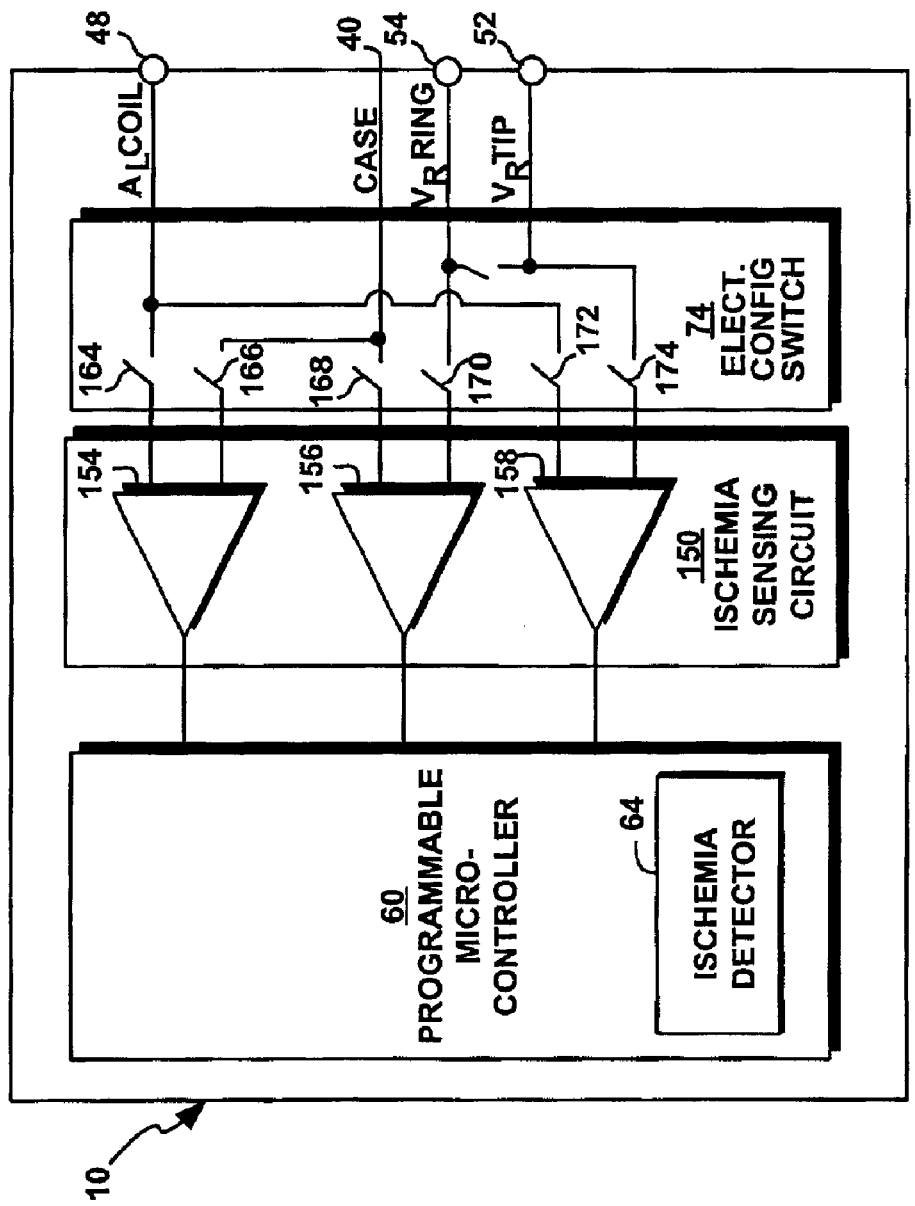
FIG. 4 is a block diagram illustrating an alternative selection of electrode combinations using shocking coil electrodes for sensing EGM signals in the detection of myocardial ischemia.

In FIG. 4, an alternative sensing configuration for the detection of myocardial ischemia is shown. In this embodiment, the left atrial shocking coil 28 located on the coronary sinus lead 24 is used for sensing the EGM signal. Since a shocking coil generally has a greater surface area then a typical pacing or sensing electrode, a shocking coil may provide a large enough surface area appropriate for myocardial ischemia detection using EGM sensing.

In other embodiments, RV coil electrode 36 could be used in place of the coupled RV tip electrode 32 and RV ring electrode 34. While specific sensing configurations are illustrated in FIGS. 3 and 4, numerous configurations may be available, depending on the leads used, for accurate and reliable sensing of the EGM signal that allows early and sensitive detection of changes in the ST-segment indicative of ischemia.

Figure 5:
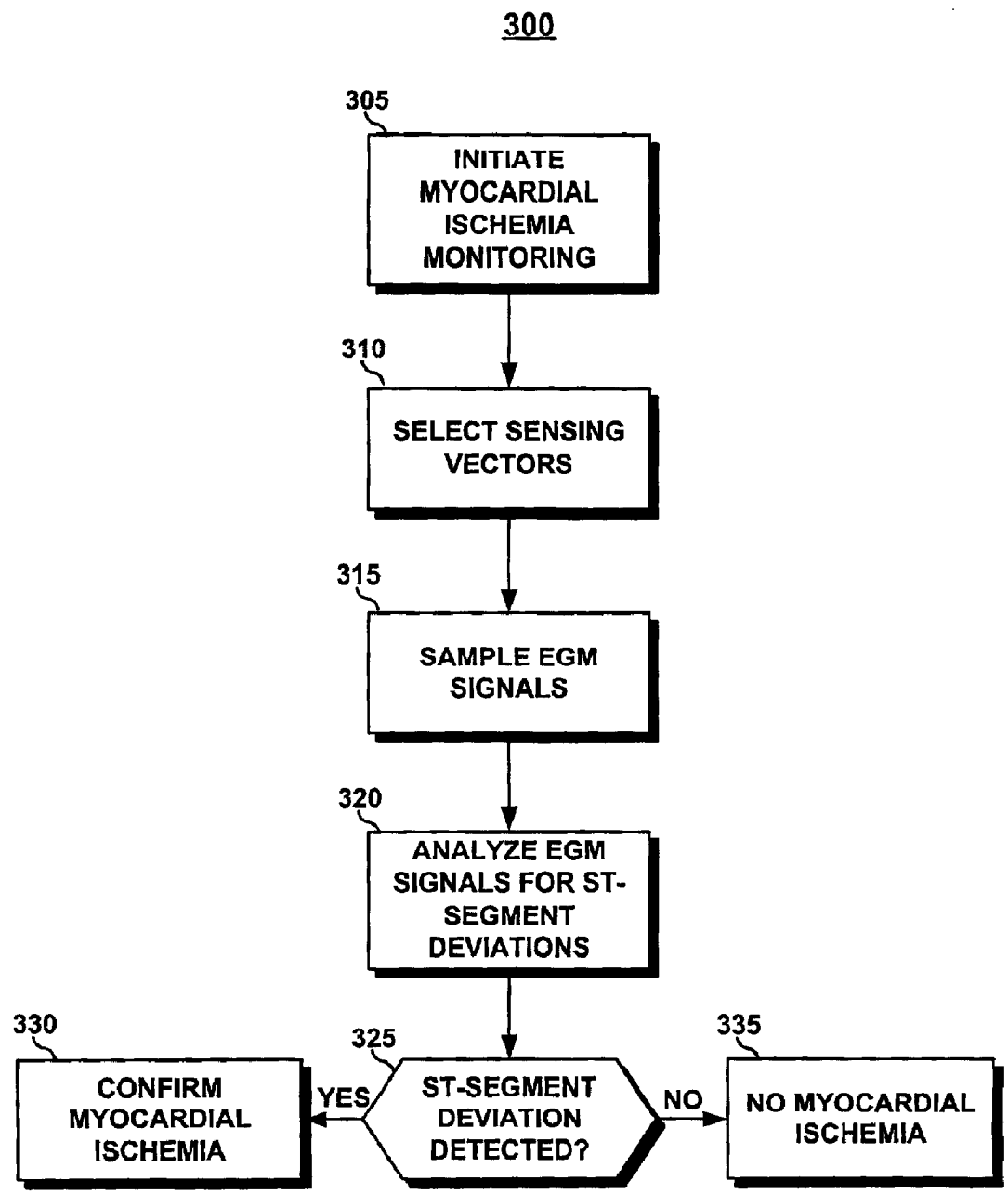
FIG. 5 is a flow chart illustrating a method of performing myocardial ischemia detection according to one embodiment.

In FIG. 5, a flow chart is shown describing an overview of the operation and novel features implemented in one embodiment of the device 10 for detecting myocardial ischemia. In this flow chart, and other flow charts presented herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The method 300 shown in FIG. 5 begins at step 305 wherein myocardial ischemia monitoring is initiated. Myocardial ischemia monitoring may be initiated whenever a change in stimulation parameters is made to increase cardiac output in response to a sensor signal. Alternatively, myocardial ischemia monitoring may be enabled by a clinician after a change in programmed operating parameters has been made. Myocardial ischemia monitoring may also be performed on a continuous or periodic basis in patients known to be susceptible to developing ischemia, e.g., patients diagnosed with coronary artery disease.

It should be clear that method 300 is applicable to patients known to be at ischemic risk at rest or activity, and is not limited to periods of adjusted stimulation parameters for increasing cardiac output, as myocardial ischemia may result from insufficient blood flow from increased metabolic demand. Accordingly, method 300 could be modified so that pacing is fixed at a low rest rate.

At step 310, the desired EGM sensing vectors are selected by connecting the appropriate electrodes to ischemia sensing circuit 150 via switch 74. This step includes the coupling of two or more electrodes located on the same lead, as described in conjunction with FIG. 3, or selecting any available coil electrodes as described in conjunction with FIG. 4, such that larger EGM sensing surface areas are available. One or more sensing vectors may be selected.

At step 315, the EGM signals from the selected sensing vector configurations are sampled by ischemia sensing circuit 150 (or alternatively data acquisition system 90). The EGM signals are then analyzed by ischemia detector 64 at step 320 to determine if a deviation in the ST-segment is present. If an ST-segment deviation is detected at decision step 325, myocardial ischemia detection is confirmed at step 330. If not, myocardial ischemia is not detected as confirmed at step 335.

According to one embodiment, the sensing vectors can be chosen by adding all the ST segments and by calculating an overall or average threshold. Myocardial ischemia changes could be in either polarity of changes. However, in order to detect "regional" ischemia, the device 10 alarms the medical attendant, or the patient, if any one or more leads exhibits a large deviation. This embodiment is analogous to an example of a patient admitted to the emergency room with chest pain, where at least two leads would be required to exhibit elevated ST deviations before more intrusive measures are taken.

Figure 6:
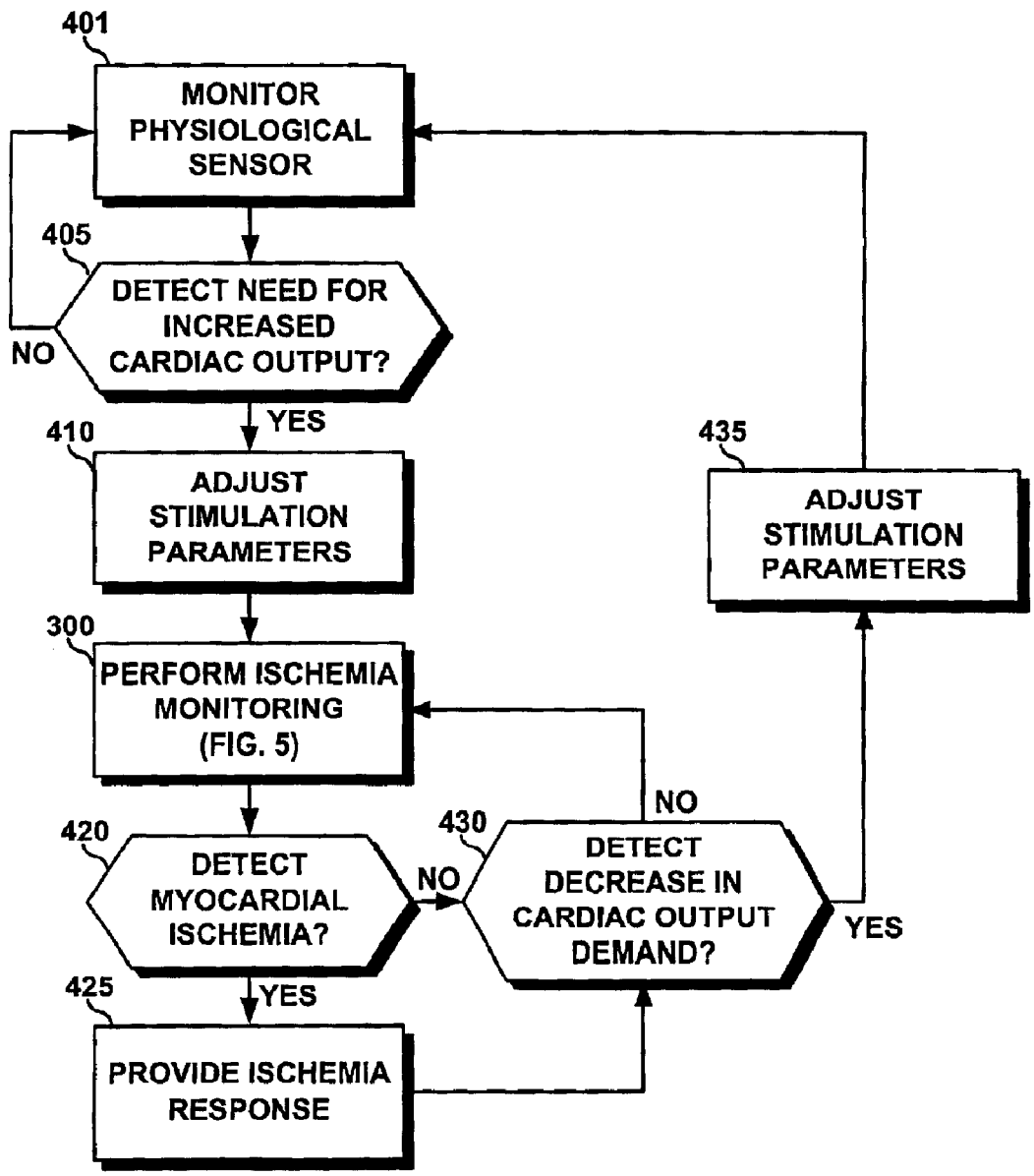
FIG. 6 is a flow chart illustrating a method of monitoring myocardial ischemia and providing a stimulation response aimed at alleviating the ischemia, according to one embodiment.

The method 400 shown in FIG. 6 illustrates one embodiment included in device 10 for detecting and responding to myocardial ischemia, using the monitoring method 300 of FIG. 5, during cardiac stimulation for the purposes of optimizing a cardiac output. Method 400 begins at step 401 by monitoring the physiological sensor 108. At step 405, microcontroller 60 determines if the signal from physiological sensor 108 indicates a suboptimal cardiac output or an increase in the patient's systemic demand requiring a higher cardiac output. If so, the device 10 stimulation parameters are adjusted at step 410 in order to increase cardiac output.

The physiologic signal monitored for determining a parameter related to cardiac output, or the systemic demand for an increased cardiac output, and the manner in which the stimulation parameters are adjusted may be in accordance with any available cardiac stimulation device intended to improve cardiac output during exercise or intrinsic heart dysfunction. For example, venous oxygen saturation may be monitored with the stimulation rate increased until venous oxygen saturation is maximized. In other embodiments, the stimulation rate may be adjusted according to a sensor-indicated rate determined from an activity sensor signal.

Therefore, in one embodiment, the methods described herein may be utilized in a device that adjusts stimulation parameters in way that optimizes cardiac output based a physiologic signal correlated to cardiac output. Such signals may include hemodynamic measures of heart performance (e.g., blood flow velocities, blood pressures, or heart chamber volumes) or metabolic measures of heart performance (e.g., blood oxygen saturation). In other embodiments, the methods described herein may be utilized in a device that adjusts stimulation parameters in a way that alters cardiac output in response to any signal correlated to cardiac output demand, i.e., the body's need for increased cardiac output. Signals related to cardiac output demand may include activity sensor signals or systemic metabolic measures, such as blood temperature, pH, or respiration, that reflect the exercise level of the patient.

When an adjustment of stimulation parameters is made at step 410, ischemia monitoring is initiated according to the method 300 presented in FIG. 5. The ST-segment of the EGM is sensed by ischemia sensing circuit 150 using the desired combination of electrodes, and the ischemia detector 64 determines at decision step 420 if myocardial ischemia has been confirmed. If so, an ischemia response is provided at step 425. In one embodiment, the ischemia response may be delayed by a short predefined period of time, e.g., 10 to 20 seconds, after which sustained ischemia is confirmed and the ischemia response is provided. The ischemia response is preferably a reduction of stimulation rate. This reduction may be a return to the programmed base stimulation rate. Alternatively, this reduction may be a stepwise reduction until myocardial ischemia is resolved as determined by continued monitoring for ischemia. In another embodiment, single chamber ventricular stimulation may be converted to biventricular stimulation. The ischemia response may include any adjustment to stimulation parameters that effectively reduces the demand placed on the myocardium.

During rate-responsive cardiac stimulation, microcontroller 60 continues to monitor physiologic sensor 108 at step 430 to determine if the demand for an increased cardiac output has decreased after providing the ischemia response, or if myocardial ischemia was not initially detected at decision step 420. If the demand for increased cardiac output remains, myocardial ischemia monitoring continues using the method 300. Then, if a decrease in cardiac output demand is determined at decision step 430, the stimulation parameters are adjusted accordingly, for example the stimulation rate may be reduced or returned to a base stimulation rate. Method 400 then returns to step 401 where microcontroller 60 continues to monitor physiological sensor 108.

Figure 8:
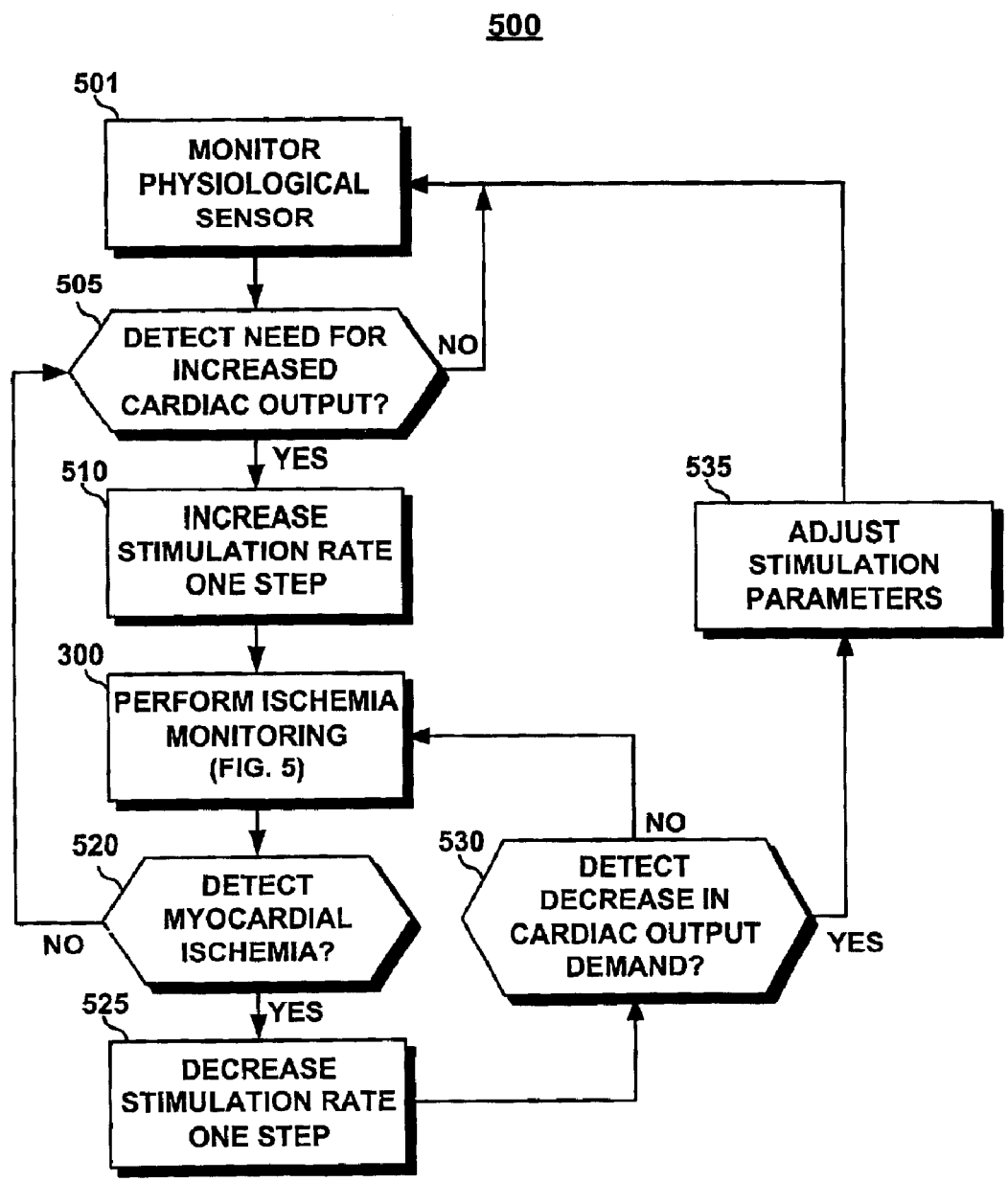
FIG. 8 is a flow chart illustrating a method of monitoring and responding to myocardial ischemia, according to one embodiment.

The flow chart shown in FIG. 8 outlines an alternative method for detecting myocardial ischemia and providing an ischemia response during adjustment of stimulation parameters for increasing cardiac output. In this embodiment, the stimulation parameter adjustment, typically stimulation rate, is increased in a stepwise fashion allowing for ischemia monitoring after each adjustment. At step 501, microcontroller 60 monitors the signal from physiologic sensor 108 and determines at decision step 505 if a need to increase cardiac output is indicated. If so, the stimulation rate is increased by one step at step 510. This step may be one programmable step or any other predefined rate increase, e.g., 10 to 20 beats per minute. If a need for increased cardiac output is not detected at decision step 505, microcontroller 60 continues to monitor physiologic sensor 108 at step 501.

After increasing the stimulation rate at step 510, myocardial ischemia monitoring is performed according to method 300 of FIG. 5. If myocardial ischemia is not detected as determined at decision step 520, the microcontroller 60 determines if a further increase in cardiac output is needed by returning to decision step 505, and, if so, the stimulation rate is again increased at step 510. Myocardial ischemia monitoring is repeated and this process continues (steps 505, 520, 300 and 520) until myocardial ischemia is detected at decision step 520.

If myocardial ischemia is detected, the stimulation rate is reduced by one step at step 525. At step 530, the microcontroller 60 determines if the demand for cardiac output has decreased as indicated by physiological sensor 108. If not, ischemia monitoring is continued according to method 300. If myocardial ischemia is still detected, at decision step 520, despite the previous reduction in stimulation rate, the stimulation rate is decreased an additional step at step 525.

This process (steps 300, 520, 525 and 530) is repeated until a decrease in the systemic cardiac output demand is detected at decision step 530 or until myocardial ischemia is no longer detected. Once the systemic cardiac output demand is decreased, the stimulation rate is reduced at step 535, and method 500 returns to step 501 where microcontroller 60 continues to monitor physiological sensor 108.

In an alternative embodiment, physiological sensor 108 additionally includes an oxygen sensor positioned in the right ventricular chamber for sensing blood oxygen saturation.

Thus, a system and method for providing sensitive and early detection of myocardial ischemia has been described in which EGM sensing using coupled electrodes or shocking coil electrodes provides larger sensing surface areas in or on the heart. In this way, the benefit provided by cardiac stimulation devices that automatically adjust stimulation parameters for optimizing cardiac output is improved by taking into account the demand placed on the myocardium and preventing ischemic injury to the heart.

While detailed descriptions of specific embodiments have been provided, it would be apparent to those reasonably skilled in the art that numerous variations of the methods described herein are possible. The descriptions provided herein are for the sake of illustration and are not intended to be exclusive.

What is claimed is:

1. In a cardiac stimulation device, a method of monitoring myocardial ischemia comprising:
   determining a sensor indicated heart rate;
   pacing at the sensor indicated heart rate;
   sensing an intracardiac electrogram signal;
   detecting myocardial ischemia based on a change in the electrogram signal; and
   in response to detecting myocardial ischemia, ignoring the sensor indicated rate and selectively adjusting one or more pacing parameters;
   wherein selectively adjusting one or more pacing parameters comprises varying an inter-ventricular timing interval.

2. In a cardiac stimulation device, a method of monitoring myocardial ischemia comprising:
   determining a sensor indicated heart rate;
   pacing at the sensor indicated heart rate;
   sensing an intracardiac electrogram signal;
   detecting myocardial ischemia based on a chance in the electrogram signal; and
   in response to detecting myocardial ischemia, ignoring the sensor indicated rate and selectively adjusting one or more pacing parameters;
   wherein selectively adjusting one or more pacing parameters comprises varying an inter-atrial timing interval.

3. In a cardiac stimulation device, a method of monitoring myocardial ischemia comprising:
   determining a sensor indicated heart rate;
   pacing at the sensor indicated heart rate;
   sensing an intracardiac electrogram signal;
   detecting myocardial ischemia based on a chance in the electrogram signal;
   in response to detecting myocardial ischemia, ignoring the sensor indicated rate and selectively adjusting one or more pacing parameters; and
   switching from a single-chamber ventricular stimulation mode to a biventricular stimulation mode;
   wherein detecting myocardial ischemia comprises detecting a deviation of an ST-segment of the cardiac electrogram signal; and
   wherein detecting the deviation of the ST-segment comprises detecting any of:
      an elevation of the ST-segment relative to a PQ-segment;
      an elevation of the ST-segment relative to a TP-segment;
      a depression of the ST-segment relative to a PQ-segment;
      a depression of the ST-segment relative to a TP-segment; and
      an inversion of a T-wave.

4. In a cardiac stimulation device, a method of monitoring myocardial ischemia comprising:
   determining a sensor indicated heart rate;
   pacing at the sensor indicated heart rate;
   sensing an intracardiac electrogram signal;
   detecting myocardial ischemia based on a change in the electrogram signal; and
   in response to detecting myocardial ischemia, ignoring the sensor indicated rate and selectively adjusting one or more pacing parameters;

wherein sensing the cardiac electrogram signal comprises electrically coupling at least two sensing electrodes to form a single sensing electrode with an expanded surface.

5. The method according to claim 4, wherein selectively adjusting one or more pacing parameters comprises varying a pacing rate.

6. The method according to claim 4, wherein sensing the intracardiac electrogram signal comprises sensing a differential signal between a coronary sinus lead electrode and a right ventricular lead electrode.

7. The method according to claim 4, wherein sensing the intracardiac electrogram signal comprises sensing a differential signal between an active electrode and a case electrode.

8. The method according to claim 4, wherein detecting myocardial ischemia comprises detecting a deviation of an ST-segment of the cardiac electrogram signal.

9. The method according to claim 8, wherein detecting the deviation of the ST-segment comprises detecting any of:
an elevation of the ST-segment relative to a PQ-segment;
an elevation of the ST-segment relative to a TP-segment;
a depression of the ST-segment relative to a PQ-segment;
a depression of the ST-segment relative to a TP-segment; and
an inversion of a T-wave.

10. The method according to claim 4, further comprising waiting for a predetermined time delay before responding to the detection of myocardial ischemia.

11. The method according to claim 4, further comprising monitoring for myocardial ischemia when the pacing parameters are automatically adjusted, in response to a physiologic signal.

12. The method according to claim 4, further comprising monitoring for myocardial ischemia on a continuous basis.

13. The method according to claim 4, further comprising monitoring for myocardial ischemia on a periodic basis in a patient known to be susceptible to myocardial ischemia.

14. The method according to claim 4, further comprising monitoring for myocardial ischemia following a user-programmed change in stimulation parameters.

15. The method of claim 4, wherein electrically coupling at least two sensing electrodes comprises temporarily shorting at least two sensing electrodes during a sensing window, within a ST segment.

16. The method of claim 15, wherein coupling at least two sensing electrodes comprises extending the ST segment for the full length of the ST segment.

17. The method according to claim 15, wherein electrically coupling at least two sensing electrodes comprises temporarily coupling at least two sensing electrodes by means of a switch.

18. The method according to claim 4, wherein electrically coupling at least two sensing electrodes comprises coupling at least two sensing electrodes on a coronary sinus lead.

19. The method according to claim 4, wherein electrically coupling at least two sensing electrodes comprises coupling at least two sensing electrodes on a right ventricular lead.

20. In a cardiac stimulation device, a method of monitoring myocardial ischemia comprising:
electrically coupling at least two sensing electrodes to form a single sensing electrode with an expanded surface;
sensing an intracardiac electrogram signal using the single sensing electrode; and
detecting myocardial ischemia based on a change in the electrogram signal.

21. The method according to claim 20, wherein electrically coupling at least two sensing electrodes comprises temporarily shorting at least two sensing electrodes during a sensing window, within a ST segment.

22. The method of claim 21, wherein coupling at least two sensing electrodes comprises extending the ST segment for the full length of the ST segment.

23. The method according to claim 21, wherein electrically coupling at least two sensing electrodes comprises coupling at least two sensing electrodes on a coronary sinus lead.

24. The method according to claim 21, wherein electrically coupling at least two sensing electrodes comprises coupling at least two sensing electrodes on a right ventricular lead.

25. The method according to claim 20, wherein electrically coupling at least two sensing electrodes comprises temporarily coupling at least two sensing electrodes by means of a switch.

26. A cardiac stimulation device that monitors myocardial ischemia, comprising:
an electrode having at least two sensing electrodes, the at least two sensing electrodes electrically coupled to form a single sensing electrode with an expanded surface;
a sensing circuit coupled to the electrode to sense an intracardiac electrogram signal;
a control circuit that determines a sensor indicated heart rate;
a pulse generator that generates stimulation pulses at the sensor indicated heart rate;
an ischemia detector, connected to the ischemia sensing circuit, that detects myocardial ischemia based on a change in the electrogram signal; and
wherein the control circuit is responsive to detection of myocardial ischemia to ignore the sensor indicated rate and to selectively adjust one or more pacing parameters.

27. The device according to claim 26, wherein the pacing parameters comprise a pacing rate.

28. The device according to claim 26, wherein the pacing parameters comprise an inter-ventricular timing interval.

29. The device according to claim 26, wherein the pacing parameters comprise an inter-atrial timing interval.

30. The device according to claim 26, wherein the change in the cardiac electrogram signal comprises a differential signal between a coronary sinus lead electrode and a right ventricular lead electrode.

31. The device according to claim 26, wherein the change in the cardiac electrogram signal comprises a differential signal between an active electrode and a case electrode.

32. The device according to claim 26, wherein the myocardial ischemia is confirmed when a deviation of an ST-segment of the cardiac electrogram signal is detected.

33. The device according to claim 32, wherein the deviation of the ST-segment comprises any of:
an elevation of the ST-segment relative to a PQ-segment;
an elevation of the ST-segment relative to a TP-segment;
a depression of the ST-segment relative to a PQ-segment;
a depression of the ST-segment relative to a TP-segment; and
an inversion of a T-wave.

34. The device according to claim 26, further comprising a switch to electrically couple the at least two sensing electrodes to form a single sensing electrode with an expanded surface.

35. The device of claim 34, wherein the switch temporarily shorts the at least two sensing electrodes during a sensing window, within a ST segment.

36. The device of claim 35, wherein the ST segment extends for substantially the length of the ST segment.

37. The device according to claim 34, wherein the at least two sensing electrodes are located on a coronary sinus lead.

38. The device according to claim 34, wherein the at least two sensing electrodes are located on a right ventricular lead.

39. A cardiac stimulation device that monitors myocardial ischemia, comprising:
    circuitry that is operative to electrically couple at least two sensing electrodes to form a single sensing electrode with an expanded surface;
    an ischemia sensing circuit that senses a cardiac electrogram signal, using the coupled electrodes; and
    an ischemia detector, connected to the ischemia sensing circuit, that detects myocardial ischemia based on a change in the electrogram signal.

40. The device according to claim 39, wherein a switch shorts the at least two sensing electrodes during a sensing window, within a ST segment.

41. The device of claim 40, wherein the ST segment extends for substantially the length of the ST segment.

42. The device according to claim 39, wherein the at least two sensing electrodes are located on any one or more of a coronary sinus lead and a right ventricular lead.

43. A cardiac stimulation device that monitors myocardial ischemia, comprising:
    means for determining a sensor indicated heart rate;
    means for pacing at the sensor indicated heart rate;
    means for coupling at least two sensing electrodes to form a single sensing electrode with an expanded surface;
    means for sensing an intracardiac electrogram signal;
    means for detecting myocardial ischemia based on a change in the electrogram signal; and
    wherein in response to detected myocardial ischemia the pacing means comprises means for ignoring the sensor indicated rate and for adjusting one or more pacing parameters.

44. The device according to claim 43, wherein the pacing parameters comprise any one or more of:
    a pacing rate;
    an inter-ventricular timing interval; and
    an inter-atrial timing interval.

45. The device according to claim 43, wherein the change in the cardiac electrogram signal comprises a differential signal between a coronary sinus lead electrode and a right ventricular lead electrode.

46. The device according to claim 43, wherein the change in the cardiac electrogram signal comprises a differential signal between an active electrode and a case electrode.

47. The device according to claim 43, wherein the myocardial ischemia is confirmed when a deviation of an ST-segment of the cardiac electrogram signal is detected.

48. The device according to claim 47, wherein the deviation of the ST-segment comprises any of:
    an elevation of the ST-segment relative to a PQ-segment;
    an elevation of the ST-segment relative to a TP-segment;
    a depression of the ST-segment relative to a PQ-segment;
    a depression of the ST-segment relative to a TP-segment; and
    an inversion of a T-wave.

49. The device according to claim 43, further comprising a switch that electrically couples the at least two sensing electrodes to form the single sensing electrode with the expanded surface.

50. The device of claim 49, wherein the switch temporarily shorts the at least two sensing electrodes during a sensing window, within a ST segment.

51. The device of claim 50, wherein the ST segment extends for substantially the length of the ST segment.

52. The device according to claim 49, wherein the at least two sensing electrodes are located on any one or more of: a coronary sinus lead and a right ventricular lead.

53. A cardiac stimulation device that monitors myocardial ischemia, comprising:
    means for electrically coupling at least two sensing electrodes to form a single sensing electrode with an expanded surface;
    means for sensing a cardiac electrogram signal, using the coupled electrodes; and
    means for detecting myocardial ischemia based on a change in the electrogram signal.

54. The device according to claim 53, further comprising a switch means to short the at least two sensing electrodes during a sensing window, within a ST segment.

55. The device of claim 54, wherein the ST segment extends for substantially the length of the ST segment.

56. The device according to claim 55, wherein the at least two sensing electrodes are located on any one or more of a coronary sinus lead and a right ventricular lead.

57. In a cardiac stimulation device, a method of monitoring myocardial ischemia comprising:
    implementing a pacing scheme;
    sensing an intracardiac electrogram signal;
    detecting myocardial ischemia based on a change in the electrogram signal; and
    in response to detecting myocardial ischemia, varying an inter-chamber timing interval in the pacing scheme.

58. The method according to claim 57, wherein varying the inter-chamber timing interval comprises varying an inter-ventricular timing interval.

59. The method according to claim 57, wherein varying the inter-chamber timing interval comprises varying an inter-atrial timing interval.

60. The method according to claim 57, wherein sensing the intracardiac electrogram signal comprises sensing a differential signal between a coronary sinus lead electrode and a right ventricular lead electrode.

61. The method according to claim 57, wherein sensing the intracardiac electrogram signal comprises sensing a differential signal between an active electrode and a case electrode.

62. The method according to claim 57, wherein detecting myocardial ischemia comprises detecting a deviation of an ST-segment of the cardiac electrogram signal by detecting any of:
    an elevation of the ST-segment relative to a PQ-segment;
    an elevation of the ST-segment relative to a TP-segment;
    a depression of the ST-segment relative to a PQ-segment;
    a depression of the ST-segment relative to a TP-segment; and
    an inversion of a T-wave.

63. The method according to claim 62, further comprising switching from a single-chamber ventricular stimulation to biventricular stimulation.

64. The method according to claim 57, further comprising waiting for a predetermined time delay before responding to the detection of myocardial ischemia.

65. The method according to claim 57, further comprising monitoring for myocardial ischemia on a continuous basis.

66. The method according to claim 57, further comprising monitoring for myocardial ischemia on a periodic basis.

67. The method according to claim 57, further comprising monitoring for myocardial ischemia following a user-programmed change in stimulation parameters.

68. The method according to claim 57, wherein sensing the intracardiac electrogram signal comprises electrically coupling at least two sensing electrodes to form a single sensing electrode.

69. The method of claim 68, wherein electrically coupling the at least two sensing electrodes comprises temporarily shorting at least two sensing electrodes.

70. The method according to claim 69, wherein electrically coupling the at least two sensing electrodes comprises temporarily coupling at least two sensing electrodes by means of a switch.

71. The method according to claim 68, wherein electrically coupling the at least two sensing electrodes comprises coupling at least two sensing electrodes on a coronary sinus lead.

72. The method according to claim 68, wherein electrically coupling the at least two sensing electrodes comprises coupling at least two sensing electrodes on a right ventricular lead.

* * * * *